United States Patent
Martinez

(10) Patent No.: US 6,592,519 B1
(45) Date of Patent: Jul. 15, 2003

(54) SMART MICROFLUIDIC DEVICE WITH UNIVERSAL COATING

(75) Inventor: Gonzalo Martinez, Mendota Heights, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/561,479

(22) Filed: Apr. 28, 2000

(51) Int. Cl.[7] ................................ A61B 5/00
(52) U.S. Cl. ............... 600/309; 600/341; 604/503; 604/66; 604/67; 604/891.1
(58) Field of Search ............ 604/890.1–891.1, 604/246, 288.01, 288.04, 503, 65–67, 19; 600/309, 317, 341, 365

(56) References Cited

U.S. PATENT DOCUMENTS

| | | |
|---|---|---|
| 3,690,769 A | 9/1972 | Mori |
| 4,114,604 A | 9/1978 | Shaw et al. |
| 4,146,029 A * | 3/1979 | Ellinwood, Jr. .......... 604/891.1 |
| 4,504,519 A | 3/1985 | Zelez |
| 4,505,799 A * | 3/1985 | Baxter ..................... 73/721 |
| 4,523,279 A | 6/1985 | Sperinde et al. |
| 4,578,173 A | 3/1986 | Seshimoto et al. |
| 4,647,362 A | 3/1987 | Watanabe |
| 4,676,847 A | 6/1987 | Lin |
| 4,750,495 A | 6/1988 | Moore et al. |
| 4,961,958 A | 10/1990 | Desphandey et al. |
| 4,981,717 A | 1/1991 | Thaler |
| 5,290,239 A * | 3/1994 | Classey et al. ...... 128/DIG. 12 |
| 5,713,923 A * | 2/1998 | Ward et al. ..................... 607/3 |
| 5,797,898 A * | 8/1998 | Santini et al. ........... 604/890.1 |
| 5,880,552 A * | 3/1999 | McGill et al. .......... 310/313 R |
| 5,995,860 A * | 11/1999 | Sun et al. .................... 600/341 |
| 6,122,536 A * | 9/2000 | Sun et al. .................... 600/317 |
| 6,203,523 B1 * | 3/2001 | Haller et al. ................ 604/131 |
| 6,227,203 B1 * | 5/2001 | Rise et al. .................... 128/898 |
| 6,233,474 B1 * | 5/2001 | Lemelson ................... 128/899 |
| 6,268,161 B1 * | 7/2001 | Han et al. ..................... 435/14 |
| 2002/0065454 A1 * | 5/2002 | Lebel et al. ................ 600/365 |

OTHER PUBLICATIONS

Analytical Chemistry, Oct. 1, 1997, pp. 69, 591A–597A, Boron–Doped Diamond Thin–Film Electrodes, Xu et al.

* cited by examiner

Primary Examiner—Gregory L. Huson
Assistant Examiner—Amanda Flynn
(74) Attorney, Agent, or Firm—Banner & Witcoff, Ltd.

(57) ABSTRACT

A medical device comprising a medical device component, the medical device component having an outer surface and an inner surface, a universal coating applied to at least the outer surface or the inner surface of the medical device component, wherein the coating is made from a material selected from the group consisting of diamond, diamond-like, borosilicate glass, carbides and nitrides. The medical device can further be a smart medical device by incorporating a sensor capable of measuring chemical and/or electrical conditions.

12 Claims, 2 Drawing Sheets

SMART MICROFLUIDIC DEVICE WITH UNIVERSAL COATING

FIELD OF INVENTION

This invention relates to "smart" medical devices that are useful for a wide variety of patient treatments, as well as methods of manufacture for these medical devices.

BACKGROUND OF THE INVENTION

Medical devices are used for drug delivery for various substances, such as morphine, Baclofen, Cisplatin, Clindamycin, Doxorubicin, Floxuridine (FUDR), Methotrexate, Heparin, Mitoxantrone, Octreotide Vinblastine, BDNF (brain derived nerve factor) etc. For example, conventional devices are specifically used to deliver morphine to cancer patients, baclofen to patients experiencing spasticity, and Floxuridine (FUDR) to patients requiring chemotherapy (e.g., most of these are treatments already approved by the FDA).

However, conventional devices have a number of disadvantages. For example, conventional devices cannot optically measure the concentrations of the drug being delivered, nor can they optically measure or monitor the patient site to be treated or being treated to ensure that the patient receives the correct amount and concentration of the drug to be delivered or being delivered at that site. Conventional devices also do not provide for optical detection or an optical trigger signal and/or system to initiate drug delivery. Thus, conventional devices are not "smart" devices because they cannot measure biological signals and/or monitor and control the concentration and amount of drug delivery.

Further, since conventional devices do not monitor the concentration and quality of the delivered drug, they cannot provide this information to a microprocessor, and thus, the microprocessor cannot analyze or control the amount and/or concentration of the drug based on that information. Conventional devices also cannot optically monitor the mixing of various substances that yield mixtures of short shelf life within these conventional devices, and thus cannot control the mixing of substances for optimum concentration of the mixed fluid to be delivered by the device to the patient.

Conventional devices can also experience corrosion due to the physical properties of substances to be delivered by these devices and the materials of conventional device components. Many of the drugs have high or low pHs that can cause severe corrosion to the components of conventional devices.

In addition, conventional devices do not have a coating suitable for a wide range of applications and delivery of various drugs (i.e., a "universal" coating), thereby leading to increased surgery to implant devices suitable for specific drugs or a limitation in the number of drugs that could be utilized in such devices.

In addition, conventional devices do not have coatings that can be easily converted into electrodes for the monitoring of electroactive analytes (e.g., organic molecules, dissolved gases, and metal ions) as well as the sensing of bioelectric events which indicate physiological function. Most conventional devices with electrodes require the utilization of separate structures with complicated interconnects (feedthroughs) welded or bonded to a substrate via harsh high temperature processes. Thus, there is a need for simpler fabrication procedures at lower temperatures for electrodes that allow three dimensional interconnection.

Further, conventional methods of manufacture of medical devices do not provide for methods of manufacture of devices having coatings useful for a wide variety of applications. For example, conventional methods of manufacture of medical devices do not provide for manufacture of coatings having optical windows for optical sensors, or selectively doped coatings to provide for monitoring of electrochemical conditions in various locations throughout the device surface, or coatings to provide corrosion resistance.

While optical sensors have been used in implantable devices to monitor oxygen in hemoglobin, optical sensors have not been used in implantable devices to monitor and control drug delivery in medical devices. Further, the optical sensors that have been used to monitor oxygen in hemoglobin comprise sapphire windows brazed onto optical sensors. Such brazing requires high temperature manual fabrication and is not well suited for microfabrication and automated manufacture.

Catheters having optical sensors could be used on a temporary basis to measure the amount of certain substances, such as nitrous oxide, in connection with temporary drug delivery. They have been used as oximeters as described in U.S. Pat. No. 4,750,495. However, conventional medical devices which are implantable are not capable of or designed to measure a large variety of concentrations or chemical conditions via optical and electrochemical sensors, and thus cannot control treatment, such as drug delivery, to a patient.

Thus, there is a great need for medical devices that overcome the above deficiencies in conventional medical devices and the methods of manufacture thereof.

SUMMARY OF THE INVENTION

A new smart medical device and methods of manufacture thereof have now been discovered that overcomes the deficiencies of conventional devices and methods of manufacture. The medical device of the present invention comprises an outer surface and an inner surface, and a coating on at least the outer surface or inner surface of the device. This construction provides a number of benefits. More specifically, in a preferred embodiment, the device has a universal coating that increases the corrosion resistance of the device, enabling the use of drugs with different chemistries, and/or enable the device to be a smart device that can monitor and control drug delivery and/or electrical stimulation therapies.

In a further preferred embodiment, the device has a coating that permits transmittance of signals, such as optical, electrochemical, electrical or thermal signals, to a sensor and/or microprocessor in the device. In a preferred embodiment, the coating is a diamond or diamond-like coating. The signals can relate to a wide variety of measurements, such as the effect of drug delivery to a specific site within a patient, or the concentration of a drug to be delivered to a patient, or the temperature at a specific site within a patient, or the electrochemical or electrical characteristics at a specific site within a patient.

In a preferred embodiment of the device of the invention, a coating is applied to at least the outer surface or the inner surface of the medical device. In another preferred embodiment, the medical device also has at least one optical sensor and a light diode. The light diode can emit light to a substance to be monitored and the optical sensor senses the light transmittance through or reflected by the substance being measured.

In another preferred embodiment of the present invention, two light diodes can be used to improve detection by reflectance. Depending on the wavelengths one can detect oxygen or other compounds in accordance with the present invention. The optical sensor can further send information regarding the sensed light to a microprocessor in the device, which will then identify the presence and concentration of the substance, and can further control the amount of drug delivery by the device based on the measurement of the substance. The drug delivery by the device can be accomplished by an electromechanical, electrochemical, solenoid or piezoelectric pump that pumps the delivered drug from a reservoir and through an catheter to a specific site within the patient. The sensor can be designed to monitor the drug chemistry and concentration prior to delivery to the patient. This is particularly useful to provide a controlled and intelligent system to mix drugs within the device, which may be desirable because of short shelf life of the mixture. The sensor can also monitor the mixing and send signals to a controller to alter the mixing, as well as change the amount of drug delivery as desired.

In another preferred embodiment of the present invention, the device can have boron doped areas on a diamond or diamond like coating that permits the transmittance of electrical signals. Such a doped area or coating can function like an ECG or EKG electrode that senses electrical potentials from cell activity. In accordance with the present invention, multiple doped areas can be fabricated in order to determine direction of bioelectric events within a patient. Additional constructions can include ion selective electrodes and other chemical/electrochemical sensors that utilize amperometric or potentiometric methods (see e.g., U.S. Pat. Nos. 4,647,362, and 4,578,173, which are incorporated herein by reference).

In another embodiment of the present invention, a coating is applied over a metallic membrane, such as a piezoelectric membrane or a transducer such as that described in U.S. Pat. No. 5,880,552 (incorporated herein by reference), for a chemical or biochemical sensor. The piezoelectric membrane can act as a sensor to measure pressure, such as blood pressure. The thin piezoelectric membrane deflects with pressure changes and it generates a small electrical signal that is proportional to the amount of deflection. The amount of deflection can in turn be correlated to the pressure (forces) acting on the piezoelectric membrane. Alternatively, a non piezoelectric material can be used as a membrane and the deflection of this material can be measured by optical methods (e.g., diode lasers) The above embodiments are particularly useful for determining when pressure is too high whereupon the device can reduce or cease drug delivery to the patient. When pressure is too low, the device will detect this as well, and initiate or increase drug delivery in an appropriate amount and manner.

In another preferred embodiment of the present invention, a coating can be used as a protective, corrosion resistant coating for a flow restrictor and/or flow diffuser used in a drug delivery catheter.

The above coatings can be made of any suitable material, including diamond and/or diamond-like materials. A diamond material comprises essentially a 100% pure diamond structure (sometimes referred to as sp3 character). A diamond-like material is a diamond material that has some other components that render the material less than essentially 100% pure diamond structure. Typically, a diamond-like structure (sometimes referred to as a mixture of sp3 and sp2) is one that is about 90% or greater pure diamond and the remainder another material (or materials), e.g., graphite.

When corrosion resistance and increased protection of the medical device components are the primary characteristics desired, the coating can be made of ceramics, oxides, metals and metal alloys, including crystalline and polycrystalline sapphire, silicon carbides, silicon nitrides, borosilicate glass (e.g., Pyrex® by Corning, Inc.), tantalum, niobium, titanium, ruthenium, hafnium, palladium, platinum, iridium, as well as their metal alloys and oxides.

The above coatings can be applied to the medical devices of the present invention in a number of ways. For example, diamond or diamond-like material can be grown onto the device by thermal processing methods, physical vapor deposition (PVD), plasma enhanced physical vapor deposition (PEPVD), and chemical vapor deposition (CVD).

Alternatively, diamond or diamond-like material can be deposited onto the device by PVD, CVD and RF plasma deposition as described in U.S. Pat. Nos. 4,981,717, 4,504,519, 5,605,759, and 5,393,572 (which are incorporated herein by reference).

A preferred method of manufacture of the present invention comprises the following steps: (1) deposit a diamond or diamond-like coating or other optically clear film on a p-type silicon wafer; (2) mask desired areas on opposite side to diamond film using suitable masking material (or thermally grow $SiO_2$) to create a pattern for desired optical windows; (3) etch (anisotropically) until reaching the diamond-like coating film (i.e., a natural etch stop process); and (4) strip off the masking material or thermally grown $SiO_2$. Each of the above steps can be easily automated and used in mass production of medical devices having the desired coating.

One objective and advantage of the present invention is the utilization of radio frequency (RF) plasma depositions to manufacture pre-assembled device components, e.g., a drug reservoir for the device, thus facilitating the manufacturing process. Electrochemical sensors fabricated with the proposed diamond or diamond like coating require much simpler fabrication procedures at lower temperatures and easy three dimensional ("3D") interconnection.

The medical devices of the present invention provide for new ways to monitor and deliver drugs with microelectromechanical devices and components. The present invention provides quality control of the drug delivery not previously attainable. The medical devices of the present invention can optically monitor sites within the patient to be treated or being treated to trigger drug delivery when needed and/or to make sure that the delivered drug is effectively treating the patient. The medical devices of the present invention can also be used to measure nitrous oxide levels within the patient, and help control blood flow and cardiac function by delivering drugs in relation to the optically or electrochemically measured nitrous oxide levels.

Objectives of the present invention include a coating for medical devices having good corrosion resistance, transparency for optical sensing, and improved processability, including microfabrication. Such a coating can be considered a "universal" coating due to the wide range of applications, corrosion resistance to a wide variety of substances, and the improved processability of such coatings onto many different medical devices for drug monitoring and delivery.

In accordance with the present invention, diamond and/or diamond-like coatings can be placed within the medical devices of the present invention to facilitate the optical measurement of the chemistry and quality of the delivered drug, as well as monitor the mixing of substances that comprise the delivered drug, and thus control the chemistry and quality of the delivered drug with a microprocessor that receives information from the sensors. More specifically, optical sensors can be placed underneath or within the diamond and diamond-like coatings to optically measure the chemistry and quality of the delivered drug within the device or outside the device where the drug is delivered to the patient.

The medical devices of the present invention can be implanted within the patient. Alternatively, the medical devices of the present invention can be used during minimally invasive surgery to deliver drugs to the patient during such surgery.

The medical devices of the present invention have numerous beneficial properties over conventional devices. The diamond and diamond like coatings of the present invention have high oxygen overpotential which makes the coating unreactive as a cathode in a galvanic couple or makes it a better electrochemical sensor by eliminating the interference of oxygen reduction on the electrode surface during potentiometric detection of chemical species, high dielectric constants, very high thermal conductivity, high hardness properties, biocompatiblity, high lubricity (better than Teflon®) and optical clarity, and thus these coatings have features and capabilities that are not provided or attainable by conventional devices. The medical device coatings of the present invention can handle acids, bases, chlorides, fluorides, and other difficult solutions without significant corrosion.

Further, medical device coatings of the present invention can be applied at relatively low temperatures, and can be used for preassembled components, thus increasing manufacturing flexibility.

The medical device coatings of the present invention can be used for fluid handling and storage applications. The medical device coatings of the present invention allow the use of optical sensors to sense concentrations in aggressive media or biological media. The medical device coatings of the present invention can also be engineered with flexible and short molecules incorporated in their molecular structure for use in curved or flexible components, for example, lead conductors.

The medical devices of the present invention can be coated with the diamond-like coatings. It is highly desirable to coat the surface of a micromachined structure at one time with a corrosion resistant coating.

Further, the coatings of the present invention can be doped with suitable material, such as boron, so that the coating becomes an electrode, and the coating can be used for electrochemical measurement and to monitor chemicals and their concentrations. For example, the clear diamond and diamond-like coatings of the present invention can be used as an optical window for a visible, infrared or near infrared sensor and these coatings can also be boron doped selectively and utilized as electrochemical sensors.

The above benefits and features of the medical devices and methods of manufacture of the present invention will be apparent to those skilled in the art.

DESCRIPTION OF THE PREFERRED EMBODIMENTS

Figure 1:
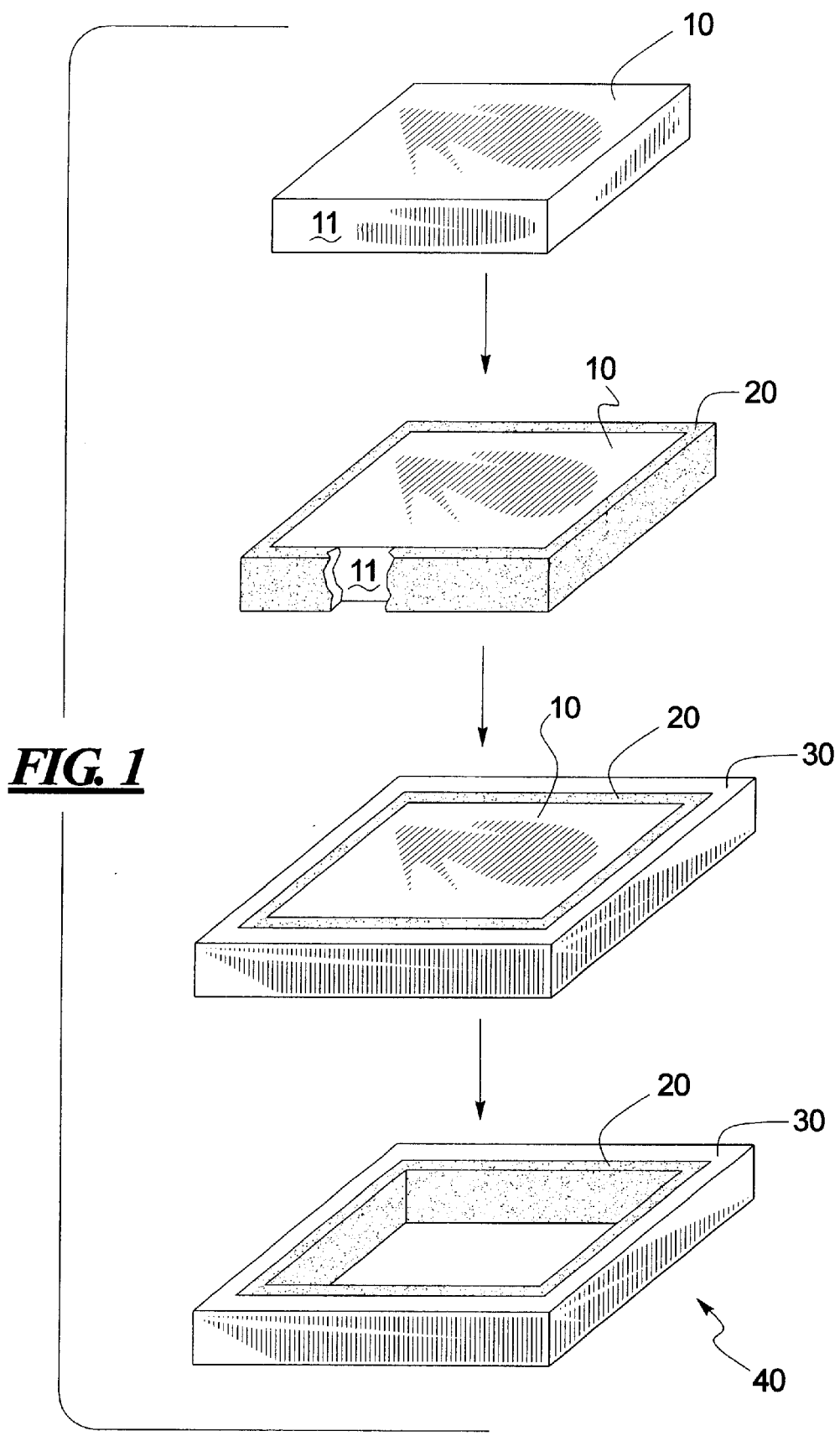
FIG. 1 illustrates a preferred method for manufacture of a preferred medical device component of the present invention.

FIG. 1 illustrates a preferred embodiment of the present invention, wherein a core 10, is formed, and then coated with a diamond or diamond-like coating 20, and then a structural support material 30 is applied to coating 20, and then the core 10 is removed, resulting in a medical device component 40, comprising structural support material 30 having a coating 20. As shown in FIG. 1, core 10 is a rectangular shaped member having a substrate surface 11. Preferably, core 10 is prepared for coating application. Methods for preparing core 10 for coating application include, but are not limited to, chemical and or mechanical polishing chemical etching, ion etching, ion milling, including the deposition of adhesion promoters, sacrificial films and/or stress relieving films. The resulting surface finish is substrate surface 11. It may be preferable to select materials so that the bond between the diamond or diamond-like coating 20 to the structural support material 30 is greater than the bond between coating 20 to core 10, so that the removal of core 10 can be made easily and still preserve the bond between coating 20 and structural support material 30. Those skilled in the art will recognize that sufficiently strong bonds between coating 20 and structural support material 30 can be achieved based on material selection and good surface preparation of structural support material 30 or coating 20, such as etching, ion milling including the deposition of adhesion promoters and intermediate films.

Preferably, coating 20 is a diamond or diamond-like coating. Coating 20 can be applied to substrate surface 11 by PVD, PEPVD or any other deposition method. This process can then be followed by thermal annealing. This method as illustrated in FIG. 1 eliminates the need for bonding diamond to diamond or DLC to DLC, which are very difficult processes.

Many sensor windows, such as optical windows, can be fabricated in accordance with the present invention by the following method. First, a diamond-like coating film is deposited on a p-type silicon wafer. Second, mask the appropriate areas on opposite side (or thermally grow silicon oxide $SiO_2$) to create a pattern for the desired window or windows. Third, etch (anisotropically) until reaching diamond-like coating film (natural etch-stop process). Fourth, strip the masking over the masked areas. This process lends itself to automatic, mass production, which reduces fabrication costs.

Another embodiment of the present invention comprises fabrication of a diamond or diamond-like coating without a bonding method. In this alternative embodiment, the diamond-like coating is applied to the substrate using a micromolding process. This process comprises fabricating a "negative" three dimensional structure substrate out of a low melting point or chemically dissolvable material (e.g., a polymer, low melting point metal, ceramic, or sol-gel), and then depositing a film of diamond-like coating, silicon coating or other coating to completely cover the substrate. Other supporting film material can be included in the support if desired. The next step in this process is to create at least one opening out of the structure (e.g., using a microdrill, laser ablade, high pressure water and/or other technique(s)) in order to melt or dissolve inside material.

The present invention provides a method of manufacture of a medical device, comprising: (a) fabricating a removable three dimensional structure, the removable three dimensional structure made from a low melting point or chemically dissolvable material; (b) depositing a universal coating onto the removable three dimensional structure, the universal coating selected from the group consisting of diamond, diamond-like, borosilicate glass (e.g., Pyrex® by Corning, Inc.), carbides, and nitrides; (c) applying a support structure to the universal coating; (d) forming an opening in the support structure and the universal coating; and (e) removing the removable three dimensional structure.

Alternatively, it is possible to design the negative three dimensional structure with two protruding nipples that can be removed (e.g., by grinding), in order to create the input and output channels to the interior of the structure. Next, the inside material is dissolved or melted. The result is a structure entirely made out of the highly corrosion resistant DLC, SiC, or other material. Further, packaging (e.g., coating, molding polymer, ceramic, metal deposition and/or plating) can be performed to give more structural stability.

The use of optical sensors previously described in the Summary of the Invention can facilitate the implementation of "smart" devices that can monitor and control the concentration and amount of drug delivery.

Figure 2:
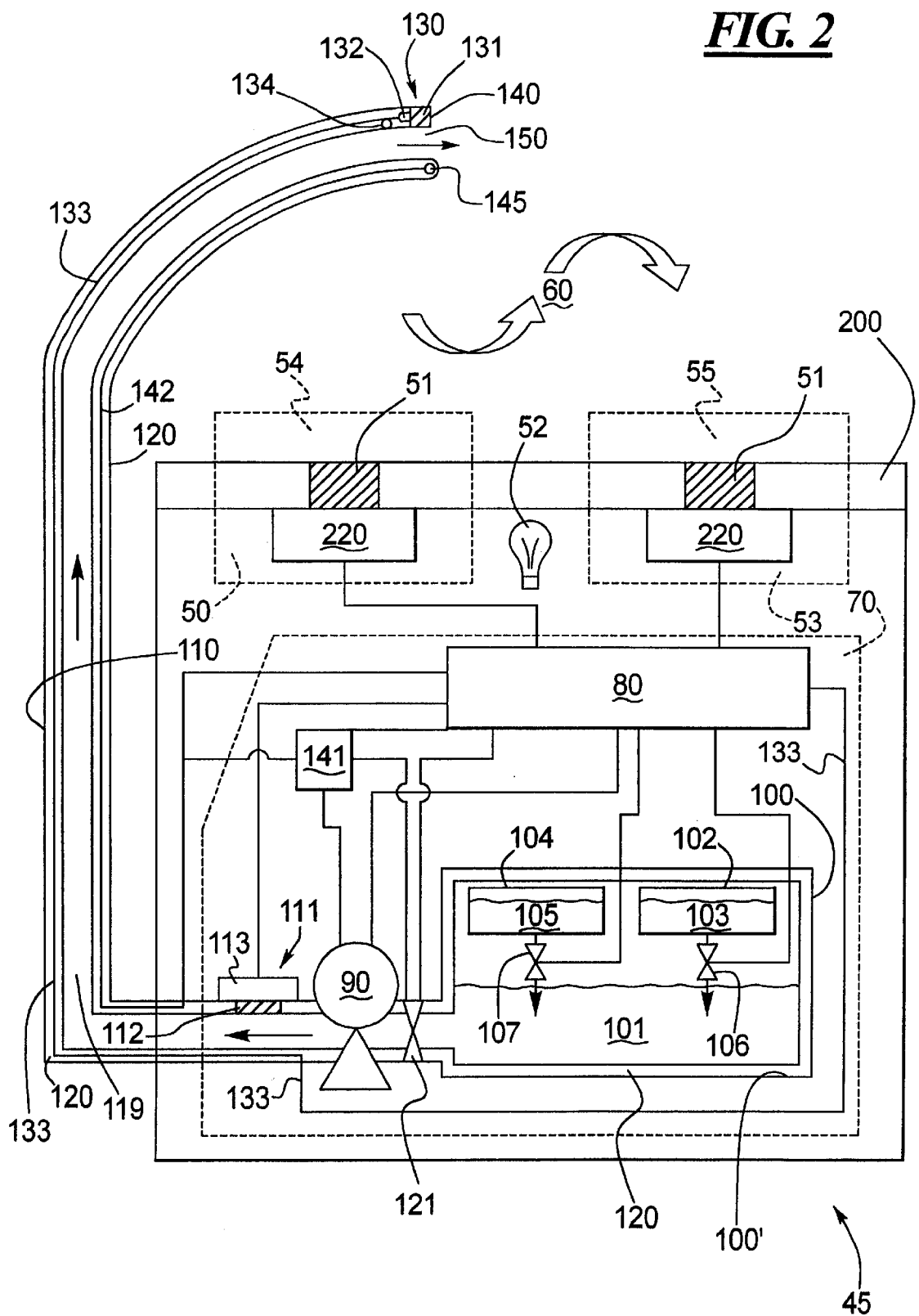
FIG. 2 illustrates a preferred embodiment of the present invention, and more particularly, a smart medical device having a coating that functions as a protective ionic/corrosion barrier and as an electrochemical or optical sensor.

An example of a smart device is a drug delivery microfluidic device 45 as shown in FIG. 2. In one preferred embodiment, microfluidic device 45 has at least one sensor 50. FIG. 2 shows a first sensor 50 and a second sensor 53, however, any number of sensors 50 and 53 may be used as desired. Sensors 50 and 53, which can be the same type of senor, can monitor the physiological condition 60 of a local area of a patient based on local chemistry, e.g., oxygen concentration, nitrous oxide, enzymes, or other optically detectable biological species. The readings by sensor 50 at a first location 54 and the readings by sensor 53 at a second location 55 can be converted to electrical signals and transmitted to a smart electronics-actuator system 70 that can deliver the required therapy to the patient based on the sensor reading. This is illustrated for a preferred embodiment in FIG. 2. Smart electronics-actuator system 70 can comprise a microprocessor 80, a pump 90, a drug reservoir 100, a reservoir effluent valve 121, and a drug delivery catheter 110, defining a drug delivery passageway 119. Drug delivery flow is shown by the arrows within drug delivery passageway 119. Microprocessor 80, pump 90, and valve 121 can be powered by power source 141. Because of the location of the sensors 50 and 53, device 45 can monitor how the drug therapy is working at first location 54 as well as at second location 55 by monitoring a bioelectric event or substance to be detected 60 at those respective locations.

Drug reservoir 100 can contain a drug 101. Drug delivery catheter 110 can have a diamond or diamond-like coating 120, and a sensor 111 that can monitor the amount, chemistry, and concentration of a drug 101 pumped by pump 90 from reservoir 100 through the drug delivery catheter 110. Diamond or diamond-like coating 120 can extend through pump 90, valve 121, and inside surface 100' of drug reservoir 100, thereby providing a protective barrier between the inside surfaces of these medical device components from drug 101. Sensor 111 shown in FIG. 2 is an electrochemical sensor. Sensor 111 can comprise a boron doped area 112, and a sputtered metal piece 113. An electrical signal from drug 101, after it is pumped by pump 90, can go through the boron doped area 112 of diamond or diamond-like coating 120. Boron doped area 112 can alternatively be made into a photon detector, which can be made of any suitable material, including but not limited to for e.g., a semiconductor, or silicon diode array. Thus, sensor 111 can "look inside" catheter 110 to monitor drug 101 amount, chemistry and concentration as drug 101 is being pumped through catheter 110. Further, sensor 111 can detect problems and electronically communicate those problems to microprocessor 80, which can then electronically control valve 121 and/or change the pumping of drug 101 by pump 90 as may be desired.

Further, this embodiment can enable in situ mixing of drug mixtures with poor shelf life and thus extend the usefulness of such drug mixtures. For example, as shown in FIG. 2, reservoir 100 can include a first pre-mix container 102 holding a first pre-mix drug 103, and a second premix container 104 holding a second pre-mix drug 105. First pre-mix container 102 can have an effluent pre-mix valve 106, and second pre-mix container 104 can have an effluent pre-mix valve 107. Pre-mix valves 106 and 107 can be in electronic communication with microprocessor 80. Thus, microprocessor 80 can adjust the mixing of pre-mix drugs 103 and 105 as may be desired based readings by sensor 111, as well as by sensor(s) 50.

Sensors 50 and 53 shown in FIG. 2, are electrochemical sensors. Sensors 50 and 53 each comprises a boron doped area 51 of a diamond or diamond-like film or coating 200, and a sputtered metal piece 220 in contact therewith. Sensors 50 and 53 can each detect the bioelectric event or substance to be detected 60, such as a biological material, a gas, or a mineral. The electrical signal from the bioelectric event or substance to be detected 60 can go through boron doped area 51 of diamond or diamond-like coating 200. Alternatively, boron doped area 51 can be made into a photon detector, which can be made of any suitable material, including but not limited to for e.g., a semiconductor, or silicon diode array.

The transmittance or reflectance of the bioelectric event or subtonic to be detected 60 can be observed using a single or multiple wavelength light source 52. Devices focusing on oxygen requirements in blood have been described (see U.S. Pat. Nos. 3,690,769; 4,523,279, 4,750,495, and 4,114,604, which are incorporated herein by reference). The sensors described in these devices use the same basic optical principle as the sensor(s) 50 of the present invention.

Alternatively, a sensor 130, similar to the sensors 111, 50 and 53 can be located at distal end 140 of catheter 110 to monitor bioelectric event or substance to be detected 60 at or near the discharge opening 150 of catheter 110. More specifically, sensor 130 can have a boron doped area 131, and a sputtered metal piece 132, and be in electrical communication with microprocessor 80 via wire 133. An electrical signal from a bioelectric event can be detected and sent to the microprocessor for analysis. The transmittance or reflectance of the bioelectric event or substance to be detected 60 can be observed by sensor 130 adapted as an optical sensor using a single or multiple wavelength light source 134.

Sensors 50, 53, 111 and 130 have been described as electrochemical sensors. These sensors can be fabricated in a number or ways to provide a boron or other type of doped areas on diamond or diamond like coating, and interconnect those doped areas to microprocessor. A fabrication method may include: 1) selective masking and 2) doping with boron as it is routinely done in the fabrication of semiconductors (see U.S. Pat. Nos. 4,961,958, and 4,676,847, which are incorporated herein by reference).

Those skilled in the art will recognize that the sensors can be a combination of any number and types of sensors in accordance with the present invention as may be desired. For example sensors 50, 53, 111, and 130 can be electrochemical and/or optical sensors.

While the device described and shown in FIG. 2 is a drug delivery device, the device can also provide electrical stimulation at electrode tip 145 at distal end 140 of catheter. Those skilled in the art will recognize that an electrical stimulation wire 142, supplied with electrical power from power source 141, can be contained within catheter 110 in place of or in addition to drug delivery passageway 119, so as to be able to provide and electrical stimulation at distal end 140. This electrical stimulation can be controlled by microprocessor 80 based on sensor readings as previously described. The electrical field from this electrical stimulation can aid the delivery of the drug by a phenomenon known as electrochemical migration. High voltage can be used to electroporate tissue thus facilitate the delivery of drugs.

Those skilled in that art will recognize that the preferred embodiments may be altered or amended without departing from the true spirit and scope of the invention, as defined in the accompanying claims. Thus, while various alterations and permutations of the invention are possible, the invention is to be limited only by the following claims and equivalents.

I claim:

1. An implantable medical device comprising: a medical device component, the medical device component having an outer surface and an inner surface, a universal coating applied to at least the outer surface or the inner surface of the medical device component, and a sensor placed between the coating and the medical device component or within the coating, the sensor capable of measuring a bioelectric event or substance to be detected, the sensor electrically connected to a microprocessor in the device, the microprocessor controlling drug delivery by the medical device.

2. The implantable medical device of claim 1 wherein the coating is made from materials selected from the group consisting of diamond, diamond-like, borosilicate glass, carbides, and nitrides.

3. The implantable medical device of claim 1 wherein the sensor is an optical sensor, the device further having a light source to emit light to a substance to be monitored by the optical device.

4. The implantable medical device of claim 1 wherein the sensor is an electrochemical sensor.

5. The implantable medical device of claim 1 wherein the sensor is a boron doped area.

6. The implantable medical device of claim 5 wherein the boron doped area is in contact with a sputtered metal piece.

7. An implantable medical device comprising:

a medical device component, the medical device component having an outer surface and an inner surface, a universal coating applied to at least the outer surface or the inner surface of the medical device component, and a sensor placed between the coating and the medical device component or within the coating, the sensor capable of measuring a bioelectric event or substance to be detected, the sensor electrically connected to a microprocessor in the device, the microprocessor controlling electrical stimulation by the medical device.

8. The medical device of claim 7 wherein the coating is made from materials selected from the group consisting of diamond, diamond-like, borosilicate glass, carbides, and nitrides.

9. The medical device of claim 7 wherein the sensor is an optical sensor, the device further having a light source to emit light to a substance to be monitored by the optical sensor.

10. The medical device of claim 7 wherein the sensor is an electrochemical sensor.

11. The implantable medical device of claim 7 wherein the sensor is a boron doped area.

12. The medical device of claim 11 wherein the boron doped area is in contact with a sputtered metal piece.

* * * * *